(12) United States Patent
Garcia

(10) Patent No.: US 9,810,064 B2
(45) Date of Patent: Nov. 7, 2017

(54) METHOD OF MONITORING UNCONVENTIONAL HYDROCARBON EXPLORATION AND DEVELOPMENT SITES

(71) Applicant: IFP Energies nouvelles, Rueil-Malmaison (FR)

(72) Inventor: Bruno Garcia, Rueil-Malmaison (FR)

(73) Assignee: IPF ENERGIES NOUVELLES, Rueil-Malmaison (FR)

( * ) Notice: Subject to any disclaimer, the term of this patent is extended or adjusted under 35 U.S.C. 154(b) by 286 days.

(21) Appl. No.: 14/670,940

(22) Filed: Mar. 27, 2015

(65) Prior Publication Data

US 2015/0285072 A1    Oct. 8, 2015

(30) Foreign Application Priority Data

Apr. 7, 2014    (FR) .................................... 14 53042

(51) Int. Cl.
| | |
|---|---|
| *E21B 49/08* | (2006.01) |
| *E21B 43/26* | (2006.01) |
| *E21B 43/16* | (2006.01) |
| *G01N 33/00* | (2006.01) |
| *G01N 33/24* | (2006.01) |
| *E21B 47/10* | (2012.01) |

(52) U.S. Cl.
CPC .......... *E21B 49/088* (2013.01); *E21B 43/168* (2013.01); *E21B 43/26* (2013.01); *E21B 47/1015* (2013.01); *G01N 33/0036* (2013.01); *G01N 33/241* (2013.01)

(58) Field of Classification Search
CPC ...... E21B 49/088; E21B 43/168; E21B 43/26; E21B 47/1015; G01N 33/0036; G01N 33/241
See application file for complete search history.

(56) References Cited

U.S. PATENT DOCUMENTS

2012/0179444 A1*    7/2012    Ganguly ................. E21B 43/26
703/10

\* cited by examiner

*Primary Examiner* — Brad Harcourt
(74) *Attorney, Agent, or Firm* — Fitch, Even, Tabin & Flannery LLP

(57) ABSTRACT

The present invention is a method of monitoring recovery site hydrocarbons (HC) using an unconventional method which permits quantifying the HC present in zones above the exploration and development zone. The method according to the invention is based on the adjustment of a model describing the gas concentration as a function of time, using in-situ geochemical analyzes of rare gases and, when appropriate, of injected gas used for fracturing, contained in fluid phases of subsoil samples. By use of rare gas analysis, the method according to the invention allows anticipation of hydrocarbon leakage above the exploration/development site.

11 Claims, 2 Drawing Sheets

METHOD OF MONITORING UNCONVENTIONAL HYDROCARBON EXPLORATION AND DEVELOPMENT SITES

CROSS REFERENCE TO RELATED APPLICATION

Reference is made to French Application Serial No. 14/53.042, filed Apr. 7, 2014, which application is incorporated herein by reference in its entirety.

BACKGROUND OF THE INVENTION

Field of the Invention

The present invention relates to unconventional hydrocarbon recovery, and more specifically to monitoring of unconventional hydrocarbon exploration and development sites.

Description of the Prior Art

Unconventional (liquid or gaseous) hydrocarbons are resources whose extraction requires a stimulation treatment in addition to the conventional drilling, as opposed to conventional hydrocarbons whose extraction requires no specific treatment apart from water and/or gas injection to increase the oil recovery yield (enhanced oil recovery EOR). Unconventional hydrocarbons thus relate to different types of resources, among which:

Shale oil is an oil trapped in the mother rock due to deep burial;

Tight oil is an oil that has managed to migrate from the mother rock but it is located in reservoirs of very low permeability;

Tight gas is the gas that has accumulated in a low-permeability reservoir like the aforementioned oil. It is generally methane in an intermediate position between shale gas and conventional gas;

Coalbed methane (CBM) is found in coal seams rich in adsorbed methane, known as firedamp in the mining industry. It is produced via simple vertical wells when natural fractures in the rock enable the release of a sufficient amount of methane to generate a significant flow rate. In the opposite case, the rock needs to be stimulated through hydraulic fracturing;

Coal mine methane (CMM) is a gas of the same nature as the previous one, which is recovered simply via pumping in old non-flooded mines, notably in France in the old seams of the Nord-Pas de Calais mining basin;

Oil shale and oil sands are organic matter that has not stayed long enough within the mother rock to be converted to hydrocarbons. Their exploitation does not require hydraulic fracturing but an extremely energy-consuming thermal treatment instead; and Shale gas is a gas that has remained trapped in the sedimentary rock at depths of 2000 to 3000 meters below the surface. The methane it comprises is contained in non-communicating micropores and it is possibly adsorbed on impermeable clay particles. The medium thus is both a mother rock and a reservoir, but this impermeability prevents extraction via conventional drilling.

Extraction of unconventional hydrocarbons, which is particularly difficult, requires systematic use of combined directional drilling and fracturing techniques, which are particularly costly. For example, the exploitation of unconventional hydrocarbons such as hydrocarbons from mother rocks (shale plays): oil shale and shale gas requires fracturing the surrounding rock in order to release these hydrocarbons. Indeed, unlike conventional natural gas that is retained within a permeable rock enabling easy exploitation, shale gas is trapped in the porosity of a rock made impermeable by the clay it contains.

For all the mother rock hydrocarbons and unconventional hydrocarbons mentioned above, the rocks are found at depths of around 2000 to 4000 m. These rocks are naturally fractured or cracked, but the fractures or cracks are closed, which does not allow a fluid to circulate and flow therethrough. The purpose of fracturing is to re-open and extend this fracture/crack network. One possible fracturing method is injecting a liquid under pressure. However, at such depths, the fractures close up again naturally and therefore, this fracture network therefore needs to be propped in such a way that it remains open for the gas and/or the oil to be able to circulate toward a producing well so as to be extracted at the surface.

These are several types of fracturing methods, such as:

Nuclear fracturing (1967), which has been abandoned but used underground detonation of an atomic bomb in order to create a fracture/crack network allowing these hydrocarbons to be exploited;

Hydraulic fracturing, a technique allowing re-opening an already naturally existing network of cracks, to extend it and thus to create a larger network. The particles (proppant) and the silica (sand) microbeads added to the fracturing water cover the walls of the fracture/crack, thus allowing the fractures/cracks created to endure and not to close up naturally. A viscosifier, a bactericide (intended to kill the bacteria possibly present) and a polymer type product are also added so that the particle-laden fluid can be circulated more easily at great depths, thus also allowing decreasing the energy consumption at the surface. Additives from the food processing industry and biodegradable products are also used. Hydraulic fracturing requires a relatively large amount of water: 10,000 to 20,000 $m^3$ water per well;

Mechanical explosive fracturing (dynamite); or

Fracturing by injecting gas such as fluoropropane (non-flammable propane) and warm helium.

Large-scale unconventional hydrocarbon development has started in the 2000s when the price of hydrocarbons rose to a lasting high level related to the conventional oil and gas production stagnation and to the world energy consumption growth. These prices, and the advances in the field of extraction techniques, have allowed financing the significant investment required for the production of a large number of wells, notably in the United States. Six-hundred thousand jobs have been created in the U.S. with the exploitation of this type of hydrocarbons. The price of coal in the United States has dropped by 30 to 40% and the price of gas has also decreased in the U.S., but not yet in the rest of the world. Furthermore, the price of oil is impacted because the United States imports less.

A risk that is often mentioned regarding the exploration and the exploitation of these unconventional hydrocarbons relates to the fact that the fracturing water (notably upon hydraulic fracturing) may conflict with water used for other purposes, such as potable water. Now, it is quite possible to use water unfit for consumption for hydraulic fracturing purposes, such as sea water (even though it generates constraints of sulfate, $H_2S$, . . . , type that can however be readily dealt with), or brackish water (salt brine).

Another important risk that is often mentioned is direct contamination through hydraulic fracturing of natural subsoil potable water. However, due to the depths at which this hydraulic fracturing is performed (notably, between 2000 and 4000 m), the risk of direct contamination is very unlikely. On the other hand, a greater risk exists along the well due to the tightness thereof.

Thus, the environmental problems related to the extraction of shale gas, notably the pollution of water reserves due to potential leakage, especially within a potable water aquifer (even though it is near zero), of hydrocarbons and of fluids injected for fracturing of the subsoil, as well as greenhouse gas emissions, have led to strong public distrust in some countries.

In order to limit these environmental problems, the monitoring of unconventional hydrocarbon recovery sites during exploration, then during and after exploitation, that is extraction of the unconventional hydrocarbons, is an important challenge for the development of this technology.

Injecting into the underground formation a tracer gas whose chemical inertia may be considered for such monitoring purposes. However, this method requires injection of a particular gas in large amounts making implementation difficult.

SUMMARY OF THE INVENTION

The present invention thus relates to a method of monitoring sites unconventional hydrocarbon recovery methods to quantify the hydrocarbons present in zones above the exploration and development zone. The method according to the invention is based on the adjustment of a model describing the gas concentration as a function of time, using in-situ geochemical analyses of rare gases and, if necessary, of injected gas used for fracturing, contained in fluid phases of subsoil samples. By means of rare gas analysis, the method according to the invention allows anticipation of hydrocarbon leakage above the exploration/development site.

The invention relates to a method of monitoring an underground formation wherein hydrocarbons are recovered with unconventional methods with at least one rare gas being present in the underground formation. The method comprises:

a) selecting a diffusion model for the rare gas and a diffusion model for a hydrocarbon to be recovered with each model describing an evolution of concentration as a function of time, of depth and of a diffusion coefficient;

b) prior to the hydrocarbon recovery, taking at least a first sample of a fluid present in a subsoil zone which is being monitored and is located above the underground formation, and measuring the composition of at least one rare gas within the first sample;

c) during and/or after the hydrocarbon recovery, taking at least a second sample of a fluid present in the subsoil zone, and measuring a concentration of the rare gas within the second sample;

d) repeating c) at different times;

e) when the concentration of the rare gas increases, modifying the diffusion coefficient of the rare gas diffusion model, to provide coherency with the measurements, and determining a ratio between the diffusion coefficient and the modified diffusion coefficient; and f) applying the ratio to the diffusion model of the hydrocarbon to be recovered, from which an amount of the hydrocarbon to be recovered present in the subsoil zone at a time t is determined.

According to the invention, the subsoil zone is an aquifer.

Advantageously, leakage of the hydrocarbon to be recovered from the underground formation is detected by the amount of hydrocarbon determined to be recovered that is present in the subsoil zone.

Preferably, the unconventional hydrocarbons are recovered by fracturing the underground formation.

Advantageously, the fracturing is performed by injecting gas such as fluoropropane or helium.

Preferably, the amount of the injected gas present in the subsoil zone at the time t is determined by a diffusion model of the injected gas, to which the ratio between the diffusion coefficient and the modified diffusion coefficient is applied.

According to an aspect of the invention, the injected gas comprises at least one rare gas.

According to an embodiment of the invention, the hydrocarbons contain methane.

Advantageously, the rare gas is helium or argon.

BRIEF DESCRIPTION OF THE DRAWINGS

Other features and advantages of the method according to the invention will be clear from reading the description hereafter of embodiments given by way of non-limitative examples, with reference to the accompanying figures wherein.

DETAILED DESCRIPTION OF THE INVENTION

The monitoring method according to the invention relates to an unconventional method of hydrocarbon exploration or development of a site.

Figure 1:
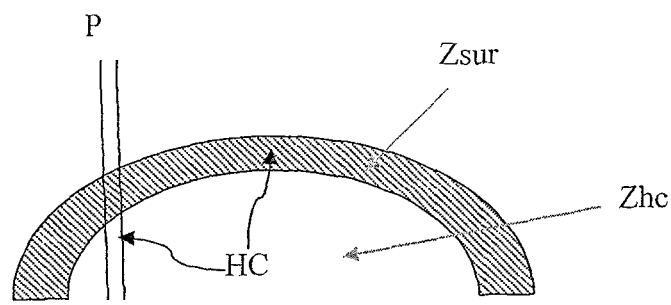
FIG. 1 illustrates an example of unconventional hydrocarbon recovery.

According to a non-limitative embodiment illustrated in FIG. 1, recovery of the unconventional hydrocarbons HC contained in an underground formation Zhc such as a particular surrounding rock, a clayey type rock of very low permeability for example, is performed via a well P. Zone Zhc which contains the hydrocarbons is topped by an upper zone, notably a water-containing aquifer. Recovery of the unconventional hydrocarbons HC requires a specific treatment, notably fracturing of underground formation Zhc. This fracturing allows recovery of the HC from well P, but it can generate migration of the hydrocarbons to the upper zone. This migration can be either advective if fracturing is excessive and poorly controlled, or diffusive, which is the case for all the sites. Diffusion being independent of permeability and depending only on porosity, even in the case of a layer of very low permeability, the diffusion phenomenon takes place. In the case of diffusion, in FIG. 1, diffusion of the hydrocarbons HC (methane $CH_4$, ethane $C_2H_6$, propane $C_3H_8$, butane $C_4H_{10}$, etc.) is symbolized by curved arrows. Methane is the predominant species in most cases and the one that diffuses the fastest among hydrocarbons because its molecule is the smallest. Diffusion to the upper zone, especially if it is an aquifer, is preferably avoided in order to limit environmental problems related to the exploitation of unconventional hydrocarbons. The method according to the invention allows monitoring this diffusion to the upper zone, referred to as a subsoil monitoring zone Zsur. Advantageously, this monitoring zone Zsur corresponds to a saline aquifer containing of non-potable water, followed by a potable water aquifer (higher (closer to the surface) in the water column).

There are several types of fracturing methods, such as: (i) injection of water under pressure (known as hydraulic fracturing), for example associated with silica (sand) microbeads to keep the created fracture open, (ii) mechanical fracturing through explosion (dynamite), or (iii) injection of gas such as fluoropropane (non-flammable propane) or warm helium (notably for drilling/fracturing in arctic regions where water freezes too fast and fluoropropane appears to be ineffective, for the same reasons).

The gas injected, fluoropropane or helium for example, used as the "fracturing agent", may also leak through diffusion and pollute the zone overlying the fractured exploited rock. This diffusion can also be prevented to limit environmental problems related to the exploitation of unconventional hydrocarbons by fracturing via gas injection.

The monitoring method according to the invention allows quantification of the hydrocarbons diffused in the upper zone and anticipation of hydrocarbon leakage to the zone by means of an analysis of the rare gases notably and possibly of the gas injected for fracturing (fluoropropane or helium for example) that are present in the upper zone. Indeed, the underground formation comprising the unconventional hydrocarbons also contains rare gases (helium or argon for example) that will also diffuse to the upper zone. Helium is naturally present in geological environments, the more so the deeper the zone. Furthermore, for fracturing via gas injection, the injected gas can also contain rare gases that will diffuse to the upper zone (notably in the case of warm helium injection).

The monitoring method is based on the use of three interesting characteristics of rare gases in relation to hydrocarbons and, when appropriate, to the injected gas:
- faster diffusion in an aqueous medium,
- finer detectability by measuring tools, and
- inactivity with respect to the environment thereof from a chemical and biological point of view.

The monitoring method essentially comprises the following stages:

1. Diffusion model selection for a rare gas and hydrocarbons
2. Rare gas concentration measurements prior to exploration and exploitation
3. Rare gas concentration measurements during exploration and after exploitation
4. Rare gas diffusion model calibration with the concentration measurements
5. Hydrocarbon diffusion model updating from the calibrated rare gas diffusion model
6. Determining the amount of hydrocarbons present in the monitoring zone at a time t from the updated model.

These stages are detailed hereafter for a non-limitative example where methane $CH_4$ is a hydrocarbon to be recovered that is contained in the underground formation. However, these stages are suited to any type of hydrocarbon contained in the underground formation, for example ethane $C_2H_6$, propane $C_3H_8$, butane $C_4H_{10}$, or mixtures thereof.

1. Diffusion Model Selection for a Rare Gas and $CH_4$

A diffusion model is selected for a rare gas, helium for example, which is naturally present in geological environments, as well as a diffusion model for a hydrocarbon, $CH_4$. Each model describes the evolution of the concentration of the chemical species as a function of time, of depth and of a diffusion coefficient specific to helium and to $CH_4$.

A 1D model of vertical migration of a constituent through diffusion is for example known, wherein the evolution of the concentration (C) of the constituent in space and in time (t) is defined by:

$$C(z, t) = C_0 erfc\left(\frac{z}{2\sqrt{Dt}}\right) \quad \text{Equation 1}$$

with:
- z being depth
- t being time
- D being effective diffusion coefficient of the constituent (rare gas, hydrocarbons, injected gas) such that D=Dm*ratio, where Dm is the molecular diffusion coefficient of the constituent and ratio (initially equal to the porosity) a parameter to be updated in stage 4 of the method,
- $C_0$ being a maximum concentration of the dissolved constituent (He or $CH_4$), i.e. the initial concentration prior to injection. It is the concentration at the water/gas interface.

According to an embodiment of the invention, where recovery of the hydrocarbons is achieved by fracturing with gas injection, a diffusion model is selected likewise for the injected gas, for example a 1D model as described in Equation 1.

Figure 2:
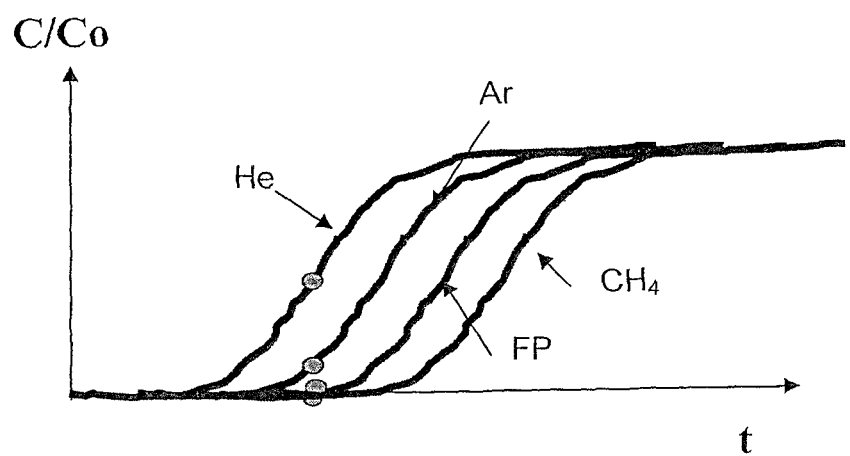
FIG. 2 illustrates helium (He), argon (Ar), fluoropropane (FP) and methane ($CH_4$) diffusion models calibrated by geochemical measurements.

FIG. 2 illustrates diffusion models (curves) for helium (He), argon (Ar), fluoropropane (FP) (gas injected for fracturing) and $CH_4$ (hydrocarbons).

2. Rare Gas Concentration Measurements Prior to Exploration/Exploitation

Prior to exploitation and exploration (considering that exploration comprises a fracturing stage), that is prior to fracturing and hydrocarbon recovery, at least a first sample of a fluid present in a monitoring zone (subsoil zone likely to be reached by the hydrocarbons) is taken and the rare gas concentration is measured within this first sample. Sampling is performed using at least one monitoring well into which a downhole sampler is run in order to recover the fluid (water) present, without disturbing the physico-chemical equilibrium of the system.

This well allows the sampler to be placed in a zone of the subsoil likely to be reached by hydrocarbons. This monitoring zone is located above the underground formation containing the hydrocarbons. It notably can be an aquifer.

A first measurement characterizing the initial state of the subsoil zone prior to exploitation is then performed on this first sample. The rare gas concentration within this first sample is measured. The concentrations of other rare gases, of the hydrocarbons and of the injected gas can also be measured if it is possible.

This stage allows constraining the compositions of the hydrocarbons (elements in gas form dissolved in the underground formation). Early detection of helium in relation to methane depends on the helium composition difference between the hydrocarbon-containing formation and the monitoring zone. Since helium is naturally present in geological environments, in a concentration which increases with depth the difference needs to be constrained by the preliminary analysis of the natural fluids.

3. Rare Gas Concentration Measurements During and after Exploitation

During and after fracturing and exploitation (hydrocarbon recovery), at least a second sample of a fluid present in the monitoring zone is taken and the rare gas concentration within this second sample is measured.

The mechanism described for the previous stage is used which is a monitoring well and downhole sampler.

This monitoring can be repeated at different times, and possibly in different monitoring wells.

A set of values relative to the ratio of the rare gas concentration at a time t during and after exploitation to the rare gas concentration prior to exploitation (one at each sampling and measuring time t) is thus obtained.

4. Rare Gas Diffusion Model Calibration with the Concentration Measurements

When the rare gas (He) concentration increases, the effective diffusion coefficient of the model selected in stage 1 is modified so that the model is coherent with the measurements. The ratio of the molecular diffusion coefficient to the modified diffusion coefficient (Equation 1) is then determined therefrom.

The simple assumption is made that the ratio is a characteristic of the medium (porosity and tortuosity) only. If several rare gases are used, an average ratio modulo one error is calculated.

FIG. 2 illustrates calibrating the analytical solution (Equation 1) that characterizes the rare gas concentration evolution as a function of time and of the position of the measuring point with the measurements performed in stage 3. The measuring points are illustrated by points in FIG. 2. FIG. 2 illustrates helium (He) and argon (Ar) diffusion models (curves) obtained by calibrating the analytical solution (Equation 1) on the measuring points. These two calibrated curves allow defining an average ratio between the molecular diffusion and the effective diffusion. This ratio allows calibration, for example, of the diffusion models (curves) of $CH_4$ and of the injected gas, fluoropropane (FP).

Figure 3:
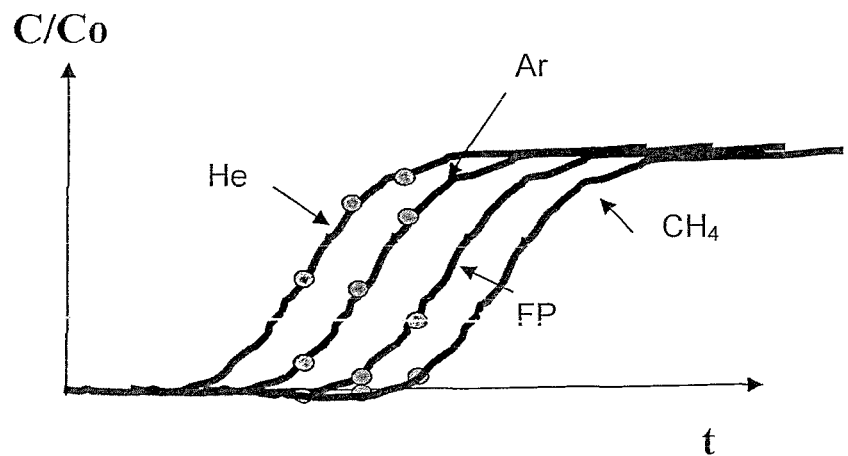
FIG. 3 illustrates the calibration improvement with subsequent geochemical measurements.

Measurements performed later allow the results to be refined by modifying the ratio (FIG. 3).

5. Hydrocarbon and Injected Gas Diffusion Model Updating

To update the $CH_4$ diffusion model from the calibrated rare gas diffusion model, the ratio calculated previously is applied to the $CH_4$ diffusion model selected in stage 1.

This ratio is therefore applied to the $CH_4$ molecular diffusion used in the $CH_4$ diffusion model selected in stage 1. A new effective $CH_4$ diffusion is thus obtained, which allows obtaining a new $CH_4$ diffusion model based on the rare gas diffusion model calibrated on experimental data in stage 4.

For the embodiment of the invention where hydrocarbon recovery is achieved by fracturing with gas injection, the injected gas diffusion model can be updated by applying the same ratio, which allows obtaining a new injected gas diffusion model based on the rare gas diffusion model calibrated on experimental data.

This stage is illustrated in FIGS. 2 and 3.

6. Determining the Amount of Hydrocarbons in the Monitoring Zone from the Updated Model In this stage, the amount of hydrocarbons present in the monitoring zone is determined at any time t in order to determine a hydrocarbon leak in the monitoring zone. The following stages are therefore carried out:
a) determining the amount of dissolved $CH_4$, and
b) determining $CH_4$ leaks.

a) Determining the Amount of Dissolved $CH_4$ at a Time t from the Updated Model The $CH_4$ diffusion model thus updated is then used to determine the amount of dissolved $CH_4$ at a time t.

Through volume integration of the model (updated Equation 1), we deduce the mass of dissolved $CH_4$ at a time t is determined by the relationship:

$$M(t) = 2\phi SMC_0 \sqrt{\frac{Dt}{\pi}} \qquad \text{Equation 2}$$

with:
$\phi$ being porosity of the medium,
S being water/gas contact surface, and
M being molar mass of $CH_4$.

b) Determining $CH_4$ Leakage into an Overlying Aquifer

According to an embodiment, it is also possible to determine injected $CH_4$ leaks from the storage zone (reservoir). According to this method, the subsoil zone, that is the zone where samples are taken from a monitoring well and a sampler, is an aquifer located above the subsoil zone into which the $CH_4$ is injected. $CH_4$ leakage out of the injection zone is detected by determining the amount of dissolved $CH_4$ in this aquifer (using the $CH_4$ diffusion model (stage 6a) of the invention).

This type of subsoil monitoring in an overlying aquifer avoids having to set up a monitoring well through the geological cover that keeps the $CH_4$ in the underground formation. Furthermore, the diffusion phenomenon is by far the predominant phenomenon within the cap rock, which is all the more interesting regarding rare gases, and therefore the method according to the invention.

This method allows quantification of the time limit provided before $CH_4$ leakage can be detected through methods and to establish leak remediation and sealing protocols. It is based on the fact that rare gases have a much lower detection threshold than $CH_4$ and they diffuse faster. The method according to the invention thus detects a $CH_4$ leak before a $CH_4$ concentration increase in the aquifer is detectable through geochemical measurement.

Figure 4:
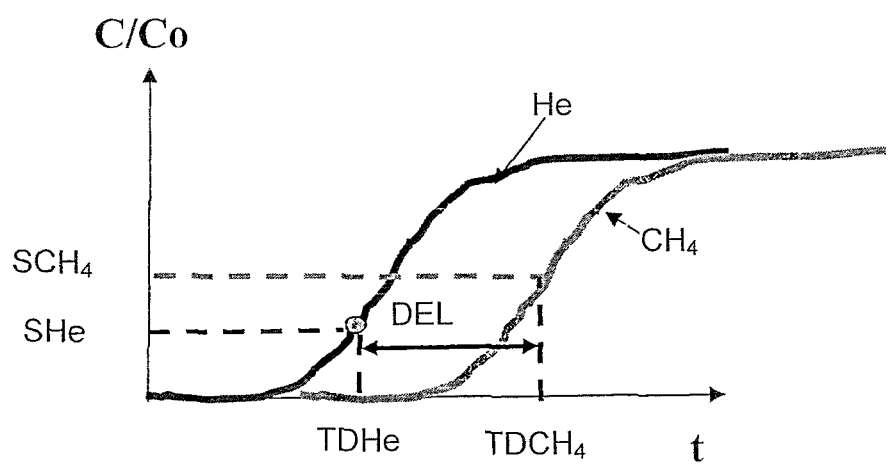
FIG. 4 illustrates the calculation of the time limit available for taking action in order to address future leakage issues.

FIG. 4 illustrates the helium and $CH_4$ diffusion models (curves) calibrated on measurements. SHe indicates the detection threshold, by geochemical measurement, of a helium concentration increase. $SCH_4$ indicates the detection threshold by geochemical measurement of a $CH_4$ concentration increase. Thus, TDHe indicates the date when a helium concentration increase is detectable and $TDCH_4$ indicates the date when a $CH_4$ concentration increase is detectable. The time limit DEL provided for taking action and fixing a potential $CH_4$ leak can then be calculated.

For the embodiment of the invention in which hydrocarbon recovery is performed by fracturing with gas injection, the amount of gas injected into the subsoil monitoring zone can be determined in order to detect an injected gas leak in the monitoring zone. This determination can be achieved using the updated injected gas diffusion model by carrying out in the same manner stages a), b) and c) described above.

Furthermore, through analysis of the injected gas used for fracturing (in considerable volume), the method according to the invention allows anticipation of a hydrocarbon leak above the exploration/development site.

Fracturing with helium injection is the method according to the invention because helium (rare gas) is injected to fracture the rock in large amount and thus, in case of leakage, the helium is present in larger amount in the monitoring zone, which allows easier and faster leak detection.

The method according to the invention is particularly suited for monitoring an underground formation from which shale oil and/or shale gas is extracted and wherein fracturing with injection of a gas such as fluoropropane or helium is performed.

The invention claimed is:

1. A method of monitoring an underground formation to recover hydrocarbons using simulation and drilling and at least one rare gas present in the underground formation, comprising:
   a) selecting a diffusion model of the at least one rare gas and a diffusion model the hydrocarbons to be recovered with each model including an evolution of concentration as a function of time and depth and a diffusion coefficient;
   b) taking at least a first sample of fluid present in a subsoil zone which is being monitored that is located above the underground formation prior to recovery of the hydrocarbons by using a downhole sampler and measuring a concentration of the at least one rare gas within the first sample of the fluid;
   c) fracturing the underground formation;
   d) at least one of during and after recovery of the hydrocarbons, taking at least a second sample of the fluid present in the subsoil zone and measuring a concentration of the at least one rare gas within at least the second sample;
   e) repeating d) at different times;
   f) determining when the concentration of the at least one rare gas increases in the at least a second sample from the concentration of the at least one rare gas in the first sample and modifying the diffusion coefficient of the diffusion model of the at least one rare gas to be coherent with the increased concentration of the at least one rare gas in the at least a second sample and determining a ratio between the diffusion coefficient before modification and the modified diffusion coefficient; and
   g) incorporating the ratio into the diffusion model of the hydrocarbons to be recovered and thereafter determining from the diffusion model of the hydrocarbons incorporating the ratio an amount of hydrocarbons in the subsoil zone that can be recovered at a time t.

2. A method as claimed in claim 1, wherein the subsoil zone is an aquifer.

3. A method as claimed in claim 1, wherein leakage of the hydrocarbons to be recovered from the underground formation is detected using an amount of the hydrocarbons which are determined to be recoverable in the subsoil zone.

4. A method as claimed in claim 2, wherein leakage of the hydrocarbons to be recovered from the underground formation is detected using an amount of the hydrocarbons which are determined to be recoverable in the subsoil zone.

5. A method as claimed in claim 1, wherein the fracturing is performed by injecting gas.

6. A method as claimed in claim 5, wherein an amount of fluoropropane which is injected into the monitoring zone or an amount of helium present in the monitoring zone at the time t is determined by incorporating the ratio into the diffusion model of the hydrocarbons.

7. A method as claimed in claim 6, wherein the injected gas comprises at least one rare gas.

8. A method as claimed in claim 5, wherein the injected gas comprises at least one rare gas.

9. A method as claimed in claim 8, wherein the at least one rare gas comprises at least one of helium and argon.

10. A method as claimed in claim 5, wherein the injected gas comprises fluoropropane or helium.

11. A method as claimed in claim 1, wherein the hydrocarbons contain methane.

* * * * *